United States Patent
Wang et al.

(10) Patent No.: US 11,633,625 B2
(45) Date of Patent: Apr. 25, 2023

(54) RADIATION THERAPY SYSTEM AND METHOD

(71) Applicant: SHANGHAI UNITED IMAGING HEALTHCARE CO., LTD., Shanghai (CN)

(72) Inventors: Peng Wang, Shanghai (CN); Cheng Ni, Shanghai (CN); Xingen Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 385 days.

(21) Appl. No.: 16/820,770

(22) Filed: Mar. 17, 2020

(65) Prior Publication Data

US 2020/0246637 A1    Aug. 6, 2020

Related U.S. Application Data

(63) Continuation of application No. PCT/CN2019/074540, filed on Feb. 2, 2019.

(51) Int. Cl.
*A61N 5/10*      (2006.01)
*A61B 5/00*      (2006.01)
(Continued)

(52) U.S. Cl.
CPC .......... *A61N 5/1049* (2013.01); *A61B 5/0036* (2018.08); *A61B 5/055* (2013.01);
(Continued)

(58) Field of Classification Search
CPC .......... A61N 5/1049; A61N 2005/1055; A61N 5/10; A61N 5/1045; A61N 2005/1052;
(Continued)

(56) References Cited

U.S. PATENT DOCUMENTS 5,235,282 A * 8/1993 Overweg ............. G01R 33/421
                                              324/318
5,708,362 A * 1/1998 Frese ................. G01R 33/3806
                                              324/319
(Continued)

FOREIGN PATENT DOCUMENTS

CN    104183355 A    12/2014
CN    105233425 A    1/2016
(Continued)

OTHER PUBLICATIONS

International Search Report in PCT/CN2019/074540 dated Aug. 28, 2019, 4 pages.
(Continued)

*Primary Examiner* — Susan S Lee
(74) *Attorney, Agent, or Firm* — Metis IP LLC

(57) ABSTRACT

The present disclosure relates to a therapeutic apparatus including an MRI apparatus configured to acquire MRI data with respect to a region of interest. The MRI apparatus may include a plurality of main magnetic field coils coaxially arranged along an axis. The MRI apparatus may also include a plurality of shielding coils arranged coaxially along the axis. A current within at least one of the shielding coils may be in the same direction with a current within the main magnetic field coils.

18 Claims, 12 Drawing Sheets

(51) Int. Cl.
*A61B 5/055* (2006.01)
*G01R 33/385* (2006.01)
*G01R 33/421* (2006.01)
*G01R 33/48* (2006.01)

(52) U.S. Cl.
CPC ..... *G01R 33/3856* (2013.01); *G01R 33/4215* (2013.01); *G01R 33/4808* (2013.01); *A61B 5/748* (2013.01); *A61N 2005/1055* (2013.01)

(58) Field of Classification Search
CPC .... A61N 2005/1061; A61N 2005/1092; A61B 5/0036; A61B 5/055; A61B 5/748; G01R 33/3856; G01R 33/4215; G01R 33/4808; G01R 33/3806; G01R 33/3815; G01R 33/421
See application file for complete search history.

(56) References Cited

U.S. PATENT DOCUMENTS

| | | | |
|---|---|---|---|
| 9,421,398 B2 | 8/2016 | Shvartsman et al. | |
| 2004/0041673 A1* | 3/2004 | Kakugawa | G01R 33/3806 335/299 |
| 2004/0169515 A1* | 9/2004 | Koga | G01R 33/3815 324/318 |
| 2005/0104590 A1 | 5/2005 | Sinnema et al. | |
| 2006/0033496 A1* | 2/2006 | Shvartsman | G01R 33/4215 324/309 |
| 2006/0082369 A1* | 4/2006 | Ariyoshi | G01R 33/3815 324/318 |
| 2009/0149735 A1 | 6/2009 | Fallone et al. | |
| 2010/0295640 A1 | 11/2010 | Tamura | |
| 2011/0012593 A1 | 1/2011 | Shvartsman et al. | |
| 2011/0196227 A1 | 8/2011 | Gross et al. | |
| 2013/0207659 A1 | 8/2013 | Ham et al. | |
| 2013/0225975 A1 | 8/2013 | Harvey | |
| 2014/0107468 A1 | 4/2014 | Calvert | |
| 2014/0121114 A1 | 5/2014 | Wang et al. | |
| 2014/0135615 A1 | 5/2014 | Kruip | |
| 2014/0221816 A1 | 8/2014 | Franke et al. | |
| 2014/0296696 A1 | 10/2014 | Remmele et al. | |
| 2015/0065860 A1 | 3/2015 | Shvartsman et al. | |
| 2016/0256712 A1 | 9/2016 | Vahala et al. | |
| 2017/0065830 A1 | 3/2017 | Vahala et al. | |
| 2017/0281043 A1 | 10/2017 | Shvartsman et al. | |
| 2017/0361128 A1 | 12/2017 | Lachaine et al. | |
| 2019/0219650 A1 | 7/2019 | Shvartsman et al. | |
| 2019/0274649 A1 | 9/2019 | Fahrig et al. | |
| 2019/0362522 A1* | 11/2019 | Han | A61B 5/0035 |
| 2021/0096197 A1* | 4/2021 | Liu | G01R 33/3815 |
| 2022/0011387 A1* | 1/2022 | Liu | G01R 33/4215 |

FOREIGN PATENT DOCUMENTS

| | | |
|---|---|---|
| CN | 107754099 A | 3/2018 |
| CN | 108014428 A | 5/2018 |
| EP | 1760482 A1 | 3/2007 |
| JP | 2004065398 A | 3/2004 |
| KR | 101378447 B1 | 3/2014 |
| KR | 20150033010 A | 4/2015 |
| KR | 20160059528 A | 5/2016 |
| WO | 2020097821 A1 | 5/2020 |

OTHER PUBLICATIONS

Written Opinion in PCT/CN2019/074540 dated Aug. 28, 2019, 4 pages.
International Search Report in PCT/CN2018/115394 dated Jul. 25, 2019, 4 pages.
Written Opinion in PCT/CN2018/115394 dated Jul. 25, 2019, 4 pages.
First Office Action in Chinese Application No. 201980005988.1 dated Jun. 7, 2021, 20 pages.

* cited by examiner

200

```
┌─────────────────────────────────────────────────────┐
│  Acquiring magnetic resonance imaging (MRI) data with│ ─── 202
│  respect to a region of interest (ROI) by an MRI     │
│  apparatus                                           │
└─────────────────────────────────────────────────────┘
                         │
                         ▼
┌─────────────────────────────────────────────────────┐
│  Reconstructing an MRI image related to at least one │ ─── 204
│  portion of the ROI based on the MRI data            │
└─────────────────────────────────────────────────────┘
                         │
                         ▼
┌─────────────────────────────────────────────────────┐
│  Determining a parameter associated with a size of the│ ─── 206
│  at least one portion of the ROI based on the MRI image│
└─────────────────────────────────────────────────────┘
                         │
                         ▼
┌─────────────────────────────────────────────────────┐
│  Generating a control signal according to the        │ ─── 208
│  parameter associated with the size of the at least  │
│  one portion of the ROI                              │
└─────────────────────────────────────────────────────┘
                         │
                         ▼
┌─────────────────────────────────────────────────────┐
│  Sending the control signal to a radiation therapy   │
│  apparatus to cause the radiation therapy apparatus  │ ─── 210
│  to apply an therapeutic radiation to the at least   │
│  one portion of the ROI                              │
└─────────────────────────────────────────────────────┘
```

FIG. 2

RADIATION THERAPY SYSTEM AND METHOD

CROSS-REFERENCE TO RELATED APPLICATIONS

This application is a Continuation of International Application No. PCT/CN2019/074540, filed on Feb. 2, 2019, the entire contents of which are hereby incorporated by reference.

TECHNICAL FIELD

The present disclosure generally relates to a radiation therapy system, and more particularly, relates to an image-guided radiation therapy system which combines radiation therapy and magnetic resonance imaging technique.

BACKGROUND

Radiation therapy on a tumor is currently affected by difficulties to track the variation (e.g., motion) of the tumor in different treatment sessions. Nowadays, various imaging techniques may be applied to provide images of the tumor before or within each treatment session. For example, a magnetic resonance imaging (MRI) apparatus may be used in combination with a radiation therapy apparatus to provide MRI images of the tumor. The combination of the MRI apparatus and the radiation therapy apparatus, which forms a therapeutic apparatus, may encounter difficulties in arranging components of the MRI apparatus (e.g., a plurality of main magnetic field coils, a plurality of magnetic shielding coils) and components of the radiation therapy apparatus (e.g., a linear accelerator) in a relatively compact space without causing interferences. For example, passive shielding technics for the radiation therapy apparatus such as providing a shielding structure surrounding the linear accelerator of the radiation therapy apparatus may have poor effect for a high intensity (e.g., 1.5 T) of the main magnetic field coils. Therefore, it may be desirable to provide a therapeutic apparatus that provides high therapeutic quality and also has a compact structure as well.

SUMMARY

According to one aspect of the present disclosure, a therapeutic apparatus including a magnetic resonance imaging (MRI) apparatus configured to acquire MRI data with respect to a region of interest (ROI) is provided. The MRI apparatus may include a main magnet body including a plurality of main magnetic field coils coaxially arranged along an axis. The MRI apparatus may also include a plurality of shielding coils including a first shielding coil, a second shielding coil and a shielding coil group arranged coaxially along the axis. The shielding coil group may be located between the first shielding coil and a second shielding coil.

In some embodiments, the shielding coil group may include a first coil group and a second coil group arranged coaxially along the axis.

In some embodiments, the first coil group or the second coil group may include a first coil and a second coil.

In some embodiments, the first coil and the second coil may be arranged concentrically.

In some embodiments, a direction of a current within the first coil may be opposite to a direction of a current within the second coil.

In some embodiments, a radius of the first coil or the second coil may be larger than that of the plurality of main magnetic field coils.

In some embodiments, a radius of the first coil may be greater than a radius of the second coil.

In some embodiments, the apparatus may further include an annular cryostat. The annular cryostat may include at least one outer wall and at least one inner wall coaxial around the axis, and an annular recess between the at least one outer wall and the at least one inner wall. The annular recess may have an opening formed at the at least one outer wall.

In some embodiments, the annular recess may be located coaxially between the first coil group and the second coil group.

In some embodiments, at least portion of the annular recess may be located radially between the first coil and the second coil.

In some embodiments, the system may further include a radiation therapy apparatus configured to apply therapeutic radiation to at least one portion of the ROI. The radiation therapy apparatus may include a linear accelerator configured to accelerate electrons in an electron beam to produce a photon beam of the therapeutic radiation. The linear accelerator may be at least partially located within the annular recess of the annular cryostat. The radiation therapy apparatus may also include one or more collimation components configured to shape the photon beam of the therapeutic radiation.

In some embodiments, at least portion of the radiation therapy apparatus may be located coaxially between the first coil group and the second coil group.

In some embodiments, at least portion of the radiation therapy apparatus may be located radially between the first coil and the second coil.

According to another aspect of the present disclosure, a magnetic resonance imaging (MRI) apparatus configured to acquire MRI data with respect to a region of interest (ROI) is provided. The MRI apparatus may include a plurality of main magnetic field coils coaxially arranged along an axis, and a plurality of shielding coils arranged coaxially along the axis. A current within at least one of the shielding coils may be in the same direction with a current within the main magnetic field coils.

In some embodiments, the shielding coils may include a first coil and a second coil with different sizes.

In some embodiments, a direction of a current within the first coil may be opposite to a direction of a current within the second coil.

In some embodiments, a radius of the first coil may be greater than a radius of the second coil which is concentric with the first coil.

In some embodiments, the direction of the current within the first coil may be the same as a direction of a current within the main magnetic field coils.

According to another aspect of the present disclosure, a therapeutic apparatus is provided. The therapeutic apparatus may include a magnetic resonance imaging apparatus configured to acquire magnetic resonance imaging data with respect to a region of interest. The magnetic resonance imaging apparatus may include an annular cryostat in which a plurality of main magnetic field coils and a plurality of shielding coils are arranged coaxially along an axis of the annular cryostat. The therapeutic apparatus may also include a radiation therapy apparatus. The radiation therapy apparatus may include a radiation source for directing therapeutic radiation to at least one portion of the region of interest. The annular cryostat may include a recess at an outer wall, and at least a portion of the radiation source is within the recess. At least one of the shielding coils may be configured to reduce the magnetic field on a region within the recess.

In some embodiments, at least one shielding coil of the shielding coils may be arranged close to a bottom of the recess, and a current within the at least one shielding coil of the shielding coils may be in an opposite direction with a current within the main magnetic field coils.

In some embodiments, at least one shielding coil of the shielding coils may be arranged close to an opening of the recess, and a current within the at least one shielding coil of the shielding coils may be in the same direction with a current within the main magnetic field coils.

In some embodiments, the shielding coils may include a first coil and a second coil with different sizes.

In some embodiments, a direction of a current within the first coil may be opposite to a direction of a current within the second coil.

In some embodiments, a radius of the first coil may be greater than a radius of the second coil which is concentric with the first coil.

In some embodiments, the direction of a current within the first coil may be the same as a direction of a current within the main magnetic field coils.

In some embodiments, at least portion of the annular recess may be located radially between the first coil and the second coil.

According to another aspect of the present disclosure, a magnetic resonance imaging (MRI) apparatus configured to acquire MRI data with respect to a region of interest (ROI) is provided. The MRI apparatus may include an annular cryostat, a plurality of main magnetic field coils coaxially arranged along an axis of the annular cryostat, at least a first pair of shielding coils and a second pair of shielding coils with different sizes. A direction of a current within the first pair of shielding coils may be opposite to a direction of a current within the main magnetic field coils. The first pair of shielding coils may be configured to shield a magnetic field outside the MRI apparatus, and the second pair of shielding coils may be configured to shield a magnetic field between the first pair of shielding coils and the main magnetic field coils.

In some embodiments, a direction of a current within the second pair of shielding coils may be the same as the direction of a current within the main magnetic field coils. The second pair of shielding coils may be close to the first pair of shielding coils.

In some embodiments, a direction of a current within the second pair of shielding coils may be opposite to the direction of a current within the main magnetic field coils. The second pair of shielding coils may be close to the main magnetic field coils.

In some embodiments, the apparatus may further include a third pair of shielding coils. A shielding coil of the third pair of shielding coils may be concentric with a shielding coil of the second pair of shielding coils.

In some embodiments, a direction of a current within the third pair of shielding coils may be opposite to a direction of a current within the second pair of shielding coils.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 is a flowchart illustrating an exemplary process for applying a therapeutic radiation in a radiation therapy system according to some embodiments of the present disclosure;

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Figure 1:
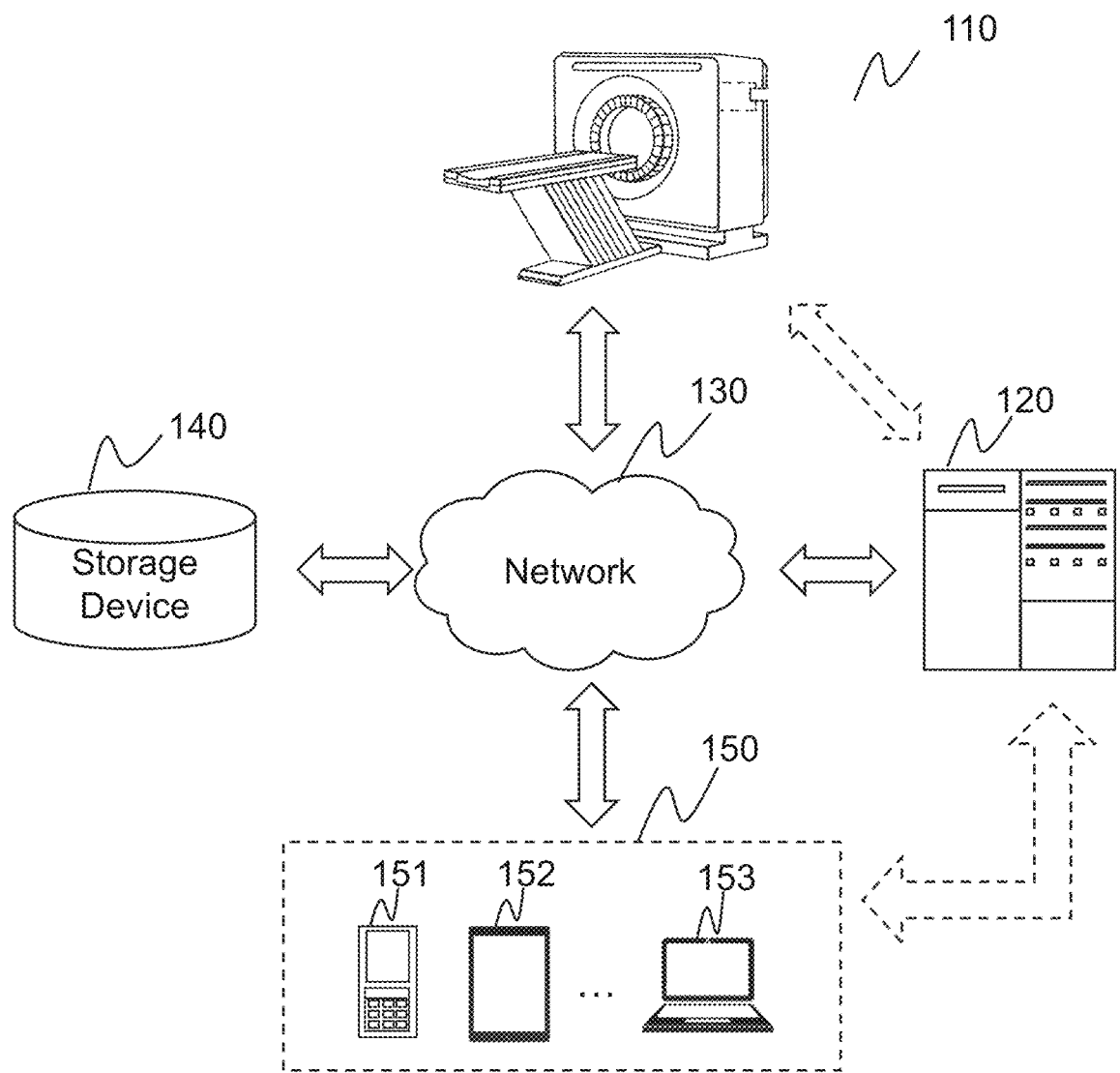
FIG. 1 is a block diagram illustrating an exemplary radiation therapy system according to some embodiments of the present disclosure.

FIG. 1 is a block diagram illustrating an exemplary radiation therapy system 100 according to some embodiments of the present disclosure. In some embodiments, the radiation therapy system 100 may be a multi-modality imaging system including, for example, a positron emission tomography-radiotherapy (PET-RT) system, a magnetic resonance imaging-radiotherapy (MRI-RT) system, etc. For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, one or more processing engines 120, a network 130, a storage device 140, and one or more terminal devices 150. In some embodiments, the therapeutic apparatus 110, the one or more processing engines 120, the storage device 140, and/or the terminal device 150 may be connected to and/or communicate with each other via a wireless connection (e.g., the wireless connection provided by the network 130), a wired connection (e.g., the wired connection provided by the network 130), or any combination thereof.

The therapeutic apparatus 110 may include a magnetic resonance imaging component (hereinafter referred to as "MRI apparatus"). The MRI apparatus may generate image data associated with magnetic resonance signals (hereinafter referred to as "MRI signals") via scanning a subject or a part of the subject. In some embodiments, the subject may include a body, a substance, an object, or the like, or any combination thereof. In some embodiments, the subject may include a specific portion of a body, a specific organ, or a specific tissue, such as head, brain, neck, body, shoulder, arm, thorax, cardiac, stomach, blood vessel, soft tissue, knee, feet, or the like, or any combination thereof. In some embodiments, the therapeutic apparatus 110 may transmit the image data via the network 130 to the one or more processing engines 120, the storage device 140, and/or the terminal device 150 for further processing. For example, the image data may be sent to the one or more processing engines 120 for generating an MRI image, or may be stored in the storage device 140.

The therapeutic apparatus 110 may also include a radiation therapy component (hereinafter referred to as "radiation therapy apparatus"). The radiation therapy apparatus may provide radiation for target region (e.g., a tumor) treatment. The radiation used herein may include a particle ray, a photon ray, etc. The particle ray may include neutron, proton, electron, μ-meson, heavy ion, α-ray, or the like, or any combination thereof. The photon ray may include X-ray, γ-ray, ultraviolet, laser, or the like, or any combination thereof. For illustration purposes, a radiation therapy apparatus associated with X-ray may be described as an example. In some embodiments, the therapeutic apparatus 110 may generate a certain dose of X-rays to perform radiotherapy under the assistance of the image data provided by the MRI apparatus. For example, the image data may be processed to locate a tumor and/or determine the dose of X-rays.

The one or more processing engines 120 may process data and/or information obtained from the therapeutic apparatus 110, the storage device 140, and/or the terminal device 150. For example, the one or more processing engines 120 may process image data and reconstruct at least one MRI image based on the image data. As another example, the one or more processing engines 120 may determine the position of the treatment region and the dose of radiation based on the at least one MRI image. The MRI image may provide advantages including, for example, superior soft-tissue contrast, high resolution, geometric accuracy, which may allow accurate positioning of the treatment region. The MRI image may be used to detect the variance of the treatment region (e.g., a tumor regression or metastasis) during the time when the treatment plan is determined and the time when the treatment is carried out, such that an original treatment plan may be adjusted accordingly. The original treatment plan may be determined before the treatment begins. For instance, the original treatment plan may be determined at least one day, or three days, or a week, or two weeks, or a month, etc., before the treatment commences.

In the original or adjusted treatment plan, the dose of radiation may be determined according to, for example, synthetic electron density information. In some embodiments, the synthetic electron density information may be generated based on the MRI image.

In some embodiments, the one or more processing engines 120 may be a single processing engine that communicates with and process data from the MRI apparatus and the radiation therapy apparatus of the therapeutic apparatus 110. Alternatively, the one or more processing engines 120 may include at least two processing engines. One of the at least two processing engines may communicate with and process data from the MRI apparatus of the therapeutic apparatus 110, and another one of the at least two processing engines may communicate with and process data from the radiation therapy apparatus of the therapeutic apparatus 110. In some embodiments, the one or more processing engines 120 may include a treatment planning system. The at least two processing engines may communicate with each other.

In some embodiments, the one or more processing engines 120 may be a single server or a server group. The server group may be centralized or distributed. In some embodiments, the one or more processing engines 120 may be local to or remote from the therapeutic apparatus 110. For example, the one or more processing engines 120 may access information and/or data from the therapeutic apparatus 110, the storage device 140, and/or the terminal device 150 via the network 130. As another example, the one or more processing engines 120 may be directly connected to the therapeutic apparatus 110, the terminal device 150, and/or the storage device 140 to access information and/or data. In some embodiments, the one or more processing engines 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components of the radiation therapy system 100 (e.g., the therapeutic apparatus 110, the one or more processing engines 120, the storage device 140, or the terminal device 150) may communicate information and/or data with one or more other components of the radiation therapy system 100 via the network 130. For example, the one or more processing engines 120 may obtain image data from the therapeutic apparatus 110 via the network 130. As another example, the one or more processing engines 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the one or more processing engines 120 and/or the terminal device 150. In some embodiments, the storage device 140 may store data and/or instructions that the one or more processing engines 120 may execute or use to perform exemplary methods described in the present disclosure. In some embodiments, the storage device 140 may include a mass storage device, a removable storage device, a cloud based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the radiation therapy system 100 (e.g., the one or more processing engines 120 or the terminal device 150). One or more components of the radiation therapy system 100 may access the data or instructions stored in the storage device 140 via the network 130. In some embodiments, the storage device 140 may be part of the one or more processing engines 120.

The terminal device 150 may be connected to and/or communicate with the therapeutic apparatus 110, the one or more processing engines 120, and/or the storage device 140. For example, the one or more processing engines 120 may acquire a scanning protocol from the terminal device 150. As another example, the terminal device 150 may obtain image data from the therapeutic apparatus 110 and/or the storage device 140. In some embodiments, the terminal device 150 may include a mobile device 151, a tablet computer 152, a laptop computer 153, or the like, or any combination thereof. For example, the mobile device 151 may include a mobile phone, a personal digital assistance (PDA), a gaming device, a navigation device, a point of sale (POS) device, a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the one or more processing engines 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the one or more processing engines 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the one or more processing engines 120 may be integrated into the therapeutic apparatus 110. However, those variations and modifications do not depart the scope of the present disclosure.

FIG. 2 is a flowchart of an exemplary process 200 for applying a therapeutic radiation by a radiation therapy system according to some embodiments of the present disclosure. In some embodiments, one or more operations of the process 200 illustrated in FIG. 2 may be implemented in the radiation therapy system 100 illustrated in FIG. 1. For example, the process 200 illustrated in FIG. 2 may be stored in the storage device 140 in the form of instructions, and invoked and/or executed by the one or more processing engines 120 illustrated in FIG. 1. For illustration purposes, the implement of the process 200 in the one or more processing engines 120 is described herein as an example. It shall be noted that the process 200 can also be similarly implemented in the terminal device 150.

In 202, the one or more processing engines 120 may acquire magnetic resonance imaging (MRI) data with respect to a region of interest (ROI) by an MRI apparatus. The MRI data may be MR signals received by an RF coil from a subject. More detailed description related to the MR signals may be found elsewhere in the present disclosure at, for example, FIG. 3 and the description thereof.

In some embodiments, an ROI may refer to a treatment region associated with a tumor. The treatment region may be a region of a subject (e.g., a body, a substance, an object). In some embodiments, the ROI may be a specific portion of a body, a specific organ, or a specific tissue, such as head, brain, neck, body, shoulder, arm, thorax, cardiac, stomach, blood vessel, soft tissue, knee, feet, or the like, or any combination thereof.

In 204, the one or more processing engines 120 may reconstruct an MRI image related to at least one portion of the ROI based on the MRI data. The MRI image may be reconstructed as a distribution of atomic nuclei inside the subject based on the MRI data. Different kinds of imaging reconstruction techniques for the image reconstruction procedure may be employed. Exemplary image reconstruction techniques may include Fourier reconstruction, constrained image reconstruction, regularized image reconstruction in parallel MRI, or the like, or a variation thereof, or any combination thereof.

The MRI image may be used to determine a therapeutic radiation to a tumor. For example, the one or more processing engines 120 may determine the position of the tumor and the dose of radiation according to the MRI image. In some embodiments, it may take at least several minutes to reconstruct an MRI image representing a large imaging region. In some embodiments, in order to generate the MRI image during a relative short time period (e.g., every second), the one or more processing engines 120 may reconstruct an initial image representing a smaller imaging region (e.g., at least one portion of the ROI) compared to that of the MRI image representing a large imaging region, and then combine the initial image with the MRI image representing a large imaging region. For example, the one or more processing engines 120 may replace a portion of the MRI image representing a large imaging region related to the ROI with the initial image. The MRI image representing a large imaging region may include information of non-ROI (e.g., a healthy tissue) near the ROI and that of the ROI. In some embodiments, the MRI image representing a large imaging region may be acquired and reconstructed before the therapeutic radiation on the tumor. For example, the MRI image representing a large imaging region may be acquired less than 1 day, or half a day, or 6 hours, or 3 hours, or 1 hour, or 45 minutes, or 30 minutes, or 20 minutes, or 15 minutes, or 10 minutes, or 5 minutes, etc., before a radiation source starts emitting a radiation beam for treatment. In some embodiments, the radiation source may include some components to generate a radiation beam. For example, the radiation source may include a linear accelerator, a target, a primary collimator and a multi-leaf collimator (MLC), etc. In some embodiments, the MRI image representing a large imaging region may be obtained from a storage device in the radiation therapy system 100, such as the storage device 140.

In 206, the one or more processing engines 120 may determine a parameter associated with a size of the at least one portion of the ROI based on the MRI image. In some embodiments, the parameter associated with a size of the at least one portion of the ROI may include the size of the cross section of a tumor which has the maximum area and is perpendicular to the direction of the radiation beams impinging on the at least one portion of the ROI. In some embodiments, the parameter associated with a size of the at least one portion of the ROI may indicate the shape of the cross section of the tumor. For example, the parameter associated with a size of at least one portion of the ROI may indicate that the shape of the cross section of the tumor is circle, and further indicate the diameter of the circle. In some embodiments, to determine the parameter associated with a size of at least one portion of the ROI, the one or more processing engines 120 may extract texture information from the MRI image, and determine texture features that are indicative of the ROI by identifying frequent texture patterns of the ROI in the extracted texture information. Then, the one or more processing engines 120 may measure the size of the region which includes the texture features in the MRI image, and determine the parameter associated with the size of the ROI.

In 208, the one or more processing engines 120 may generate a control signal according to the parameter associated with the size of at least one portion of the ROI. The control signal may be dynamically adjusted based on the plurality of MRI images taken at different time points. In some embodiments, the control signal may include parameters associated with the therapeutic radiation on the tumor. For example, the control signal may include the dosage of X-rays and a duration of the radiation beam. For another example, the control signal may include parameters of multi-leaf collimator (MLC) that determines the shape of the radiation beam projected on the subject. The MLC may include a plurality of individual leaves of high atomic numbered materials (e.g., tungsten) moving independently in and out of the path of the radiation beam. In some embodiments, the control signal may include parameters associated with movements of one or more components of a radiation therapy apparatus. For example, the control signal may include a parameter associated with one or more positions of a radiation source of the radiation therapy apparatus (e.g., the radiation therapy apparatus in the therapeutic apparatus 110, a radiation therapy apparatus 300). For another example, the control signal may include a parameter associated with a height or a position of a platform of the radiation therapy apparatus (e.g., a location of the platform 308 of the treatment table 330 along an axis of the main magnetic body 302) to properly position a patient so that the treatment region (e.g., a cancerous tumor or lesion) in the patient may properly receive the radiation beam from the radiation therapy apparatus.

In 210, the one or more processing engines 120 may send the control signal to a radiation therapy apparatus to cause the radiation therapy apparatus to apply the therapeutic radiation. During the therapeutic radiation, the radiation source of the radiation therapy apparatus may rotate, and the dosage of X-rays, duration of radiation beam from a radiation source, the shape of MLC and the position of the platform may be varied. In some embodiments, the radiation beam may be emitted only when the radiation source of the radiation therapy apparatus rotates to certain angles (e.g., 60 degrees, 120 degrees, 180 degrees, 240 degrees, 300 degrees, 360 degrees). For example, an intensity modulated radiation therapy (IMRT) may be applied. The radiation source may stop rotating intermittently. The radiation source may rotate to a desired position, pause there, and emit a radiation beam, and then resume to rotate. In some embodiments, the radiation source may rotate continuously, and emit a radiation beam continuously or intermittently. In some embodiments, the radiation source may continuously emit the radiation beam while rotating.

In some embodiments, as described above, a treatment region (e.g., a region including a tumor) may be determined according to the image data acquired from the MRI apparatus. Then a radiation beam may be generated by a radiation source of the radiation therapy apparatus to perform the therapeutic radiation to the treatment region. For example, the dosage of the radiation beam and/or the position of the treatment region may be determined in real-time with the assistance of the MRI apparatus.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 202 and 204 may be performed simultaneously.

Figure 3A:
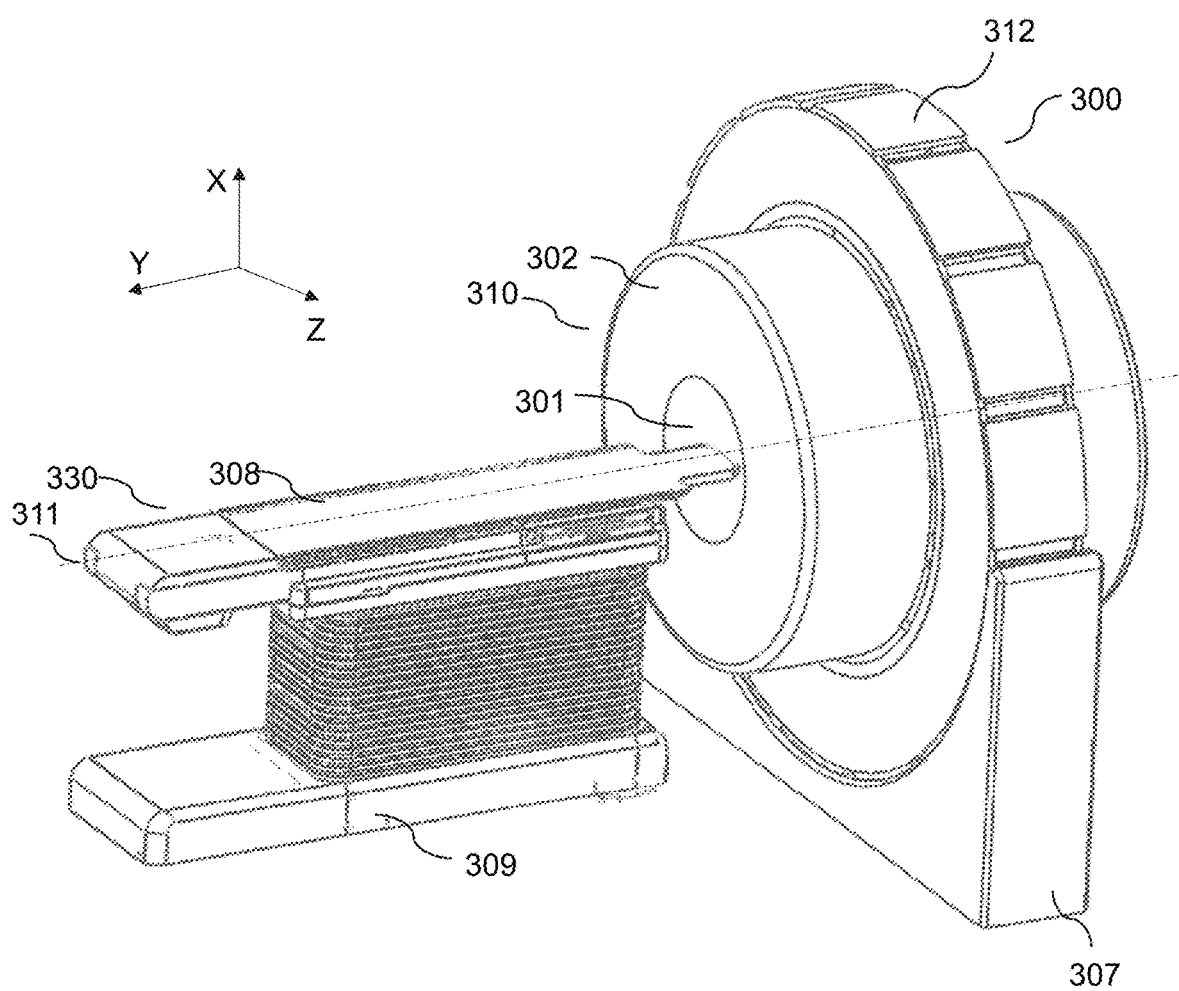
FIG. 3A illustrates an exemplary therapeutic apparatus according to some embodiments of the present disclosure.

FIG. 3A illustrates an exemplary therapeutic apparatus 110 according to some embodiments of the present disclosure. As illustrated in FIG. 3A, the therapeutic apparatus 110 may include an MRI apparatus 310, a radiation therapy apparatus 300, and a treatment table 330. In some embodiments, the MRI apparatus 310 may generate the MRI data as described in connection with operation 202, and the radiation therapy device 300 may apply the therapeutic radiation as described in connection with operation 210.

The MRI apparatus 310 may include a bore 301, a main magnetic body 302, one or more gradient coils (not shown), and one or more radiofrequency (RF) coils (not shown). The MRI apparatus 310 may be configured to acquire image data from an imaging region. For example, the image data may relate to the treatment region associated with a tumor. In some embodiments, the MRI apparatus 310 may be a permanent magnet MRI scanner, a superconducting electromagnet MRI scanner, or a resistive electromagnet MRI scanner, etc., according to the types of the main magnetic body 302. In some embodiments, the MRI apparatus 310 may be a high-field MRI scanner, a mid-field MRI scanner, and a low-field MRI scanner, etc., according to the intensity of the magnetic field. In some embodiments, the MRI apparatus 310 may be of a closed-bore (cylindrical) type, an open-bore type, or the like.

The main magnetic body 302 may have the shape of an annulus and may generate a static magnetic field B0. The main magnetic body 302 may be of various types including, for example, a permanent magnet, a superconducting electromagnet, a resistive electromagnet, etc. The superconducting electromagnet may include niobium, vanadium, technetium alloy, etc.

The one or more gradient coils may generate magnetic field gradients to the main magnetic field B0 in the X, Y, and/or Z directions (or axes). In some embodiments, the one or more gradient coils may include an X-direction (or axis) coil, a Y-direction (or axis) coil, a Z-direction (or axis) coil, etc. For example, the Y-direction coil may be designed based on a circular (Maxwell) coil, the Z-direction coil and the X-direction coil may be designed on the basis of the saddle (Golay) coil configuration. As used herein, the Z direction may also be referred to as the readout (RO) direction (or a frequency encoding direction), the X direction may also be referred to as the phase encoding (PE) direction, the Y direction may also be referred to as the slice-selection encoding direction. In the present disclosure, the readout direction and the frequency encoding direction may be used interchangeably.

Merely by way of example, the gradient magnetic fields may include a slice-selection gradient field corresponding to the Y-direction, a phase encoding (PE) gradient field corresponding to the X-direction, a readout (RO) gradient field corresponding to the Z-direction, etc. The gradient magnetic fields in different directions may be used to encode the spatial information of MR signals. In some embodiments, the gradient magnetic fields may also be used to perform at least one function of flow encoding, flow compensation, flow dephasing, or the like, or any combination thereof.

The one or more RF coils may emit RF pulses to and/or receive MR signals from a subject (e.g., a body, a substance, an object) being examined. As used herein, an RF pulse may include an excitation RF pulse and a refocusing RF pulse. In some embodiments, the excitation RF pulse (e.g., a 90-degree RF pulse) may tip magnetization vector away from the direction of the main magnetic field B0. In some embodiments, the refocusing pulse (e.g., a 180-degree RF pulse) may rotate dispersing spin isochromatic about an axis in the transverse plane so that magnetization vector may rephase at a later time. In some embodiments, the RF coil may include an RF transmitting coil and an RF receiving coil. The RF transmitting coil may emit RF pulse signals that may excite the nucleus in the subject to resonate at the Larmor frequency. The RF receiving coil may receive MR signals emitted from the subject. In some embodiments, the RF transmitting coil and RF receiving coil may be integrated into one single coil, for example, a transmitting/receiving coil. The RF coil may be one of various types including, for example, a quotient difference (QD) orthogonal coil, a phase-array coil, etc. In some embodiments, different RF coils 240 may be used for the scanning of different parts of a body being examined, for example, a head coil, a knee joint coil, a cervical vertebra coil, a thoracic vertebra coil, a temporomandibular joint (TMJ) coil, etc. In some embodiments, according to its function and/or size, the RF coil may be classified as a volume coil and a local coil. For example, the volume coil may include a birdcage coil, a transverse electromagnetic coil, a surface coil, etc. As another example, the local coil may include a solenoid coil, a saddle coil, a flexible coil, etc.

The radiation therapy device 300 may include a drum 312 and a base 307. The drum 312 may have the shape of an annulus. The drum 312 may be disposed around the main magnetic body 302 and intersect the main magnetic body 302 at a central region of the main magnetic body 302 along the axis 311 of the bore 301. The drum 312 may accommodate and support a radiation source that is configured to emit a radiation beam towards the treatment region in the bore 301. The radiation beam may be an X-ray beam, an electron beam, a proton ray source, etc. The drum 312, together with the radiation source mounted thereon, may be able to rotate around the axis 311 of the bore 301 and/or a point called the isocenter. Merely by way of example, the drum 312, together with the radiation source mounted thereon, may be able to rotate any angle, e.g., 90 degrees, 180 degrees, 360 degrees, 450 degrees, 540 degrees, around the axis 311. The drum 306 may be further supported by the base 307.

It should be noted that the above description is merely provided for the purposes of illustration, and not intended to limit the scope of the present disclosure. For persons having ordinary skills in the art, multiple variations or modification may be made under the teaching of the present disclosure. For example, the radiation therapy device 300 may further include a linear accelerator configured to accelerate electrons, ions, or protons, a dose detecting device, a temperature controlling device (e.g., a cooling device), a multiple layer collimator, or the like, or any combination thereof.

However, those variations and modifications do not depart from the scope of the present disclosure.

The treatment table 330 may include a platform 308 and a base frame 309. In some embodiments, the platform 308 may move along the horizontal direction and enter into the bore 301 of the MRI apparatus 310. In some embodiments, the platform 308 may move two-dimensionally, three-dimensionally, four-dimensionally, five-dimensionally or six-dimensionally. In some embodiments, the platform 308 may move according to the variance (e.g., position change) of the tumor estimated by, for example, a real-time MRI image obtained during a treatment.

In some embodiments, the subject may be placed on the platform 308 and sent into the MRI device. In some embodiments, the subject may be a human patient. The human patient may lie on the back, lie in prone, lie on the side on the platform 308.

During the treatment, the drum 312 may be set to rotate around the main magnetic body 302. In some embodiments, the main magnetic body 302 may include a recess (not shown) at its outer wall. The recess may be disposed around the entire circumference of the main magnetic body 302. For example, the recess may have the shape of an annulus surrounding the main magnetic body 302, thus accommodating at least part of the drum 312. In some embodiments, the recess may be disposed around part of the circumference of the main magnetic body 302. For example, the recess may have the shape of one or more arcs around the main magnetic body 302.

In some embodiments, at least a portion of the radiation source is within the recess. This arrangement may reduce the distance between the radiation source and the axis 311 of the bore 301 along the radial direction of the main magnetic body 302. In some embodiments, the radiation source may move along an entire path of rotation within the recess. In some embodiments, the radiation source may move along a path of rotation within the recess that is not an entire circle, such as a semicircle or ¾ circle or ⅘ circle. Under such situation, the radiation source will move clockwise and then anti-clockwise during treatment, and the table may also move. The radiation source may generate the radiation beam according to one or more parameters. Exemplary parameter may include a parameter of the radiation beam, a parameter of the radiation source, or a parameter of the platform 308. For example, the parameter of the radiation beam may include an irradiating intensity, an irradiating angle, an irradiating distance, an irradiating area, an irradiating time, an intensity distribution, or the like, or any combination thereof. The parameter of the radiation source may include a position, a rotating angle, a rotating speed, a rotating direction, the configuration of the radiation source, or the like, or any combination thereof. In some embodiments, the generation of the radiation beam by the radiation source may take into consideration energy loss of the radiation beam due to, e.g., the main magnetic body 302 located in the pathway of the radiation beam that may absorb at least a portion of the radiation beam. For example, the irradiating intensity of the radiation beam may be set larger than that in the situation in which there is no energy loss due to, e.g., the absorption by the main magnetic body 302 accordingly to compensate the energy loss such that the radiation beam of a specific intensity may impinge on a treatment region (e.g., a tumor).

Figure 3B:
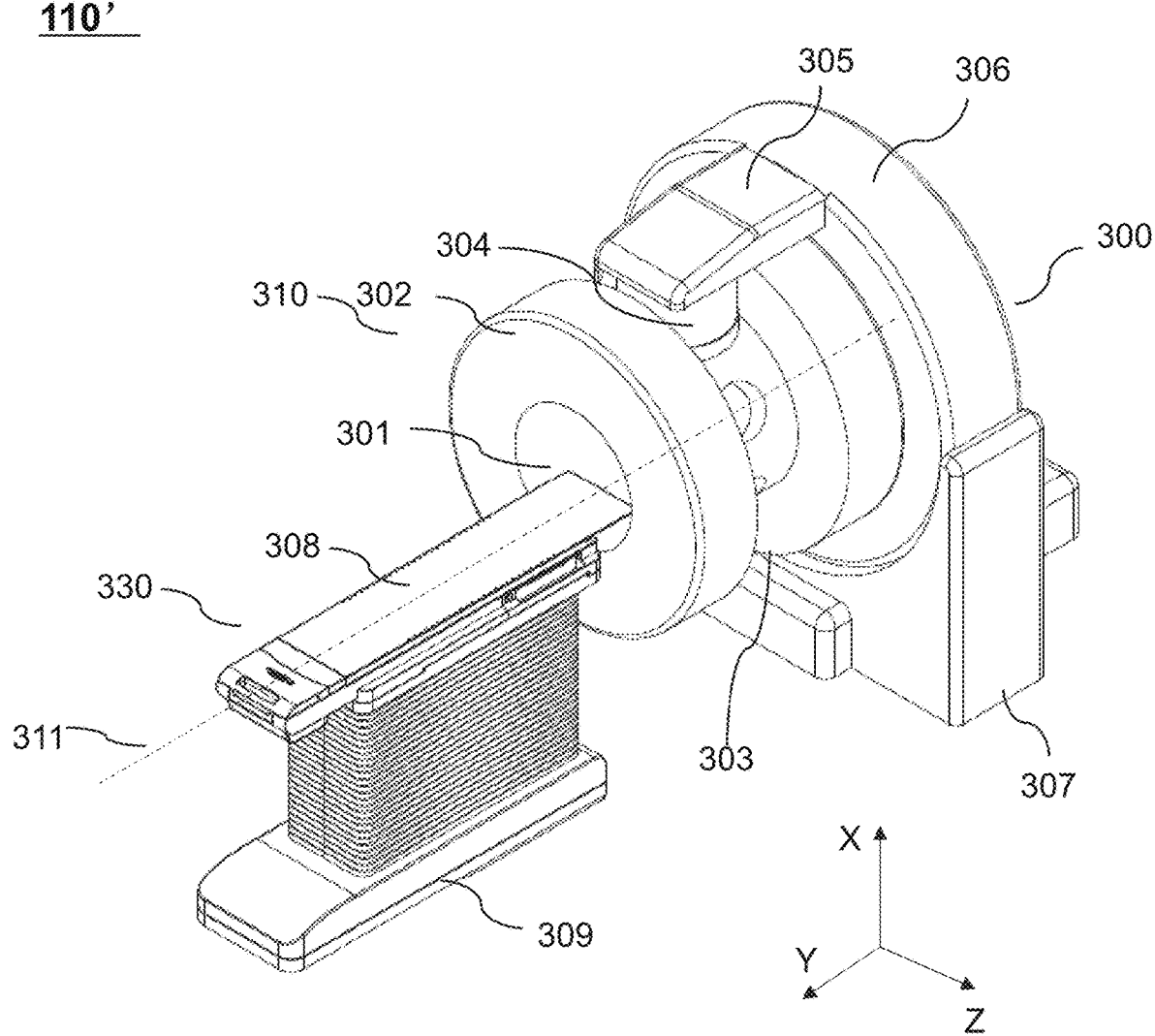
FIG. 3B illustrates another exemplary therapeutic apparatus according to some embodiments of the present disclosure.

FIG. 3B illustrates another exemplary therapeutic apparatus 110' according to some embodiments of the present disclosure. Compared with the therapeutic apparatus 110 described in FIG. 3A, the therapeutic apparatus 110' may use a gantry 306 instead of the drum 312. The gantry 306 may be disposed at one side of the main magnetic body 302. A treatment head 304 may be installed on the gantry 306 via a treatment arm 305. The treatment head 304 may accommodate the radiation source. The gantry 306 may be able to rotate the treatment head 304 around the axis 311 of the bore 301.

As shown in FIG. 3B, a recess 303 may be formed at the outer wall of the main magnetic body 302 and have the shape of an annulus. The recess 303 may accommodate at least a portion of the treatment head 304 and provide a path for rotation of the treatment head 304. This arrangement may reduce the distance between the treatment head 304 and the axis 311 of the bore 301 along the radial direction of the main magnetic body 302. In some embodiments, the reduction of the distance between the treatment head 304 and the axis 311 of the bore 301 may cause an increase of the radiation dose that may reach the treatment region (e.g., a tumor) which leads to an enhancement in the therapeutic efficiency. In some embodiments, the width of the recess 303 along the Y direction (i.e., the axial direction of the main magnetic body 302) may be no less than the width of the treatment head 304 along the Y direction.

It should be noted that the above description of the therapeutic apparatus 110 is merely provided for the purposes of illustration, and not intended to limit the scope of the present disclosure. For persons having ordinary skills in the art, multiple variations and modifications may be made under the teachings of the present disclosure. For example, the assembly and/or function of the therapeutic apparatus 110 may vary or change according to a specific implementation scenario. In some embodiments, the main magnetic body 302 of the MRI apparatus 310 may also rotate relative to the treatment head 304. For example, the radiation therapy device 300 and the MRI apparatus 310 may synchronously or asynchronously rotate around a same axis (e.g., the axis 311). However, those variations and modifications do not depart from the scope of the present disclosure.

Figure 4A:
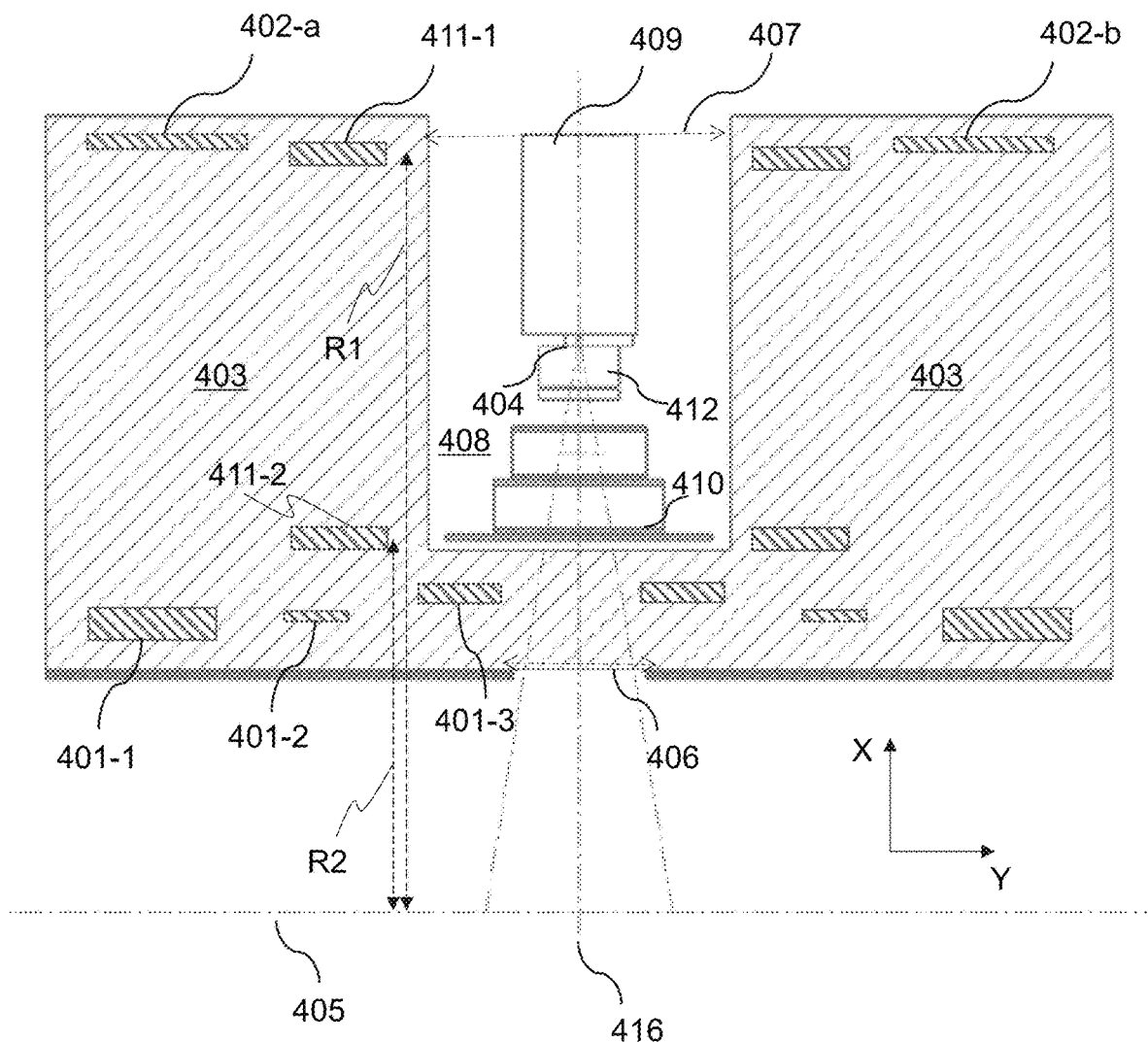
FIG. 4A shows an upper portion of a cross-sectional view of an exemplary therapeutic apparatus viewed along the Z direction according to some embodiments of the present disclosure.

FIG. 4A shows an upper portion of a cross-sectional view of an exemplary therapeutic apparatus 400 viewed along the Z direction according to some embodiments of the present disclosure. The therapeutic apparatus 400 may include an MRI apparatus that is configured to generate MRI data and a radiation therapy apparatus that is configured to apply therapeutic radiation.

As shown in FIG. 4A, the MRI apparatus may include a plurality of main magnetic field coils 401 (e.g., first main magnetic field coils 401-1, second main magnetic field coils 401-2, third main magnetic field coils 401-3), a plurality of shielding coils (e.g., shielding coils 402, shielding coils 411-1, shielding coils 411-2), and a cryostat 403. The shielding coils 402 may include a first pair of shielding coils with a first size, i.e., a first shielding coil 402-a and a second shielding coil 402-b. The shielding coils 411-1 may include a second pair of shielding coils with a second size. The shielding coils 411-2 may include a third pair of shielding coils with a third size. The first size, the second size and the third size may be different from each other. The shielding coils 411-1 (i.e., the second pair of shielding coils) may be close to the shielding coils 402 (i.e., the first pair of shielding coils). In some embodiments, the shielding coils 411-1 (also referred to as first coils) and the shielding coils 411-2 (also referred to as second coils) may also be referred as a shielding coil group 411.

The plurality of main magnetic field coils 401, the shielding coils 402 and the shielding coil group 411 may be accommodated in the cryostat 403 and maintained in the superconductive state under a certain condition (e.g., when both the coils are merged in a cooling medium in the cryostat 403).

The cryostat 403 may have the shape of an annulus with an axis 405 (e.g., the axis 311 in FIG. 3A). The plurality of main magnetic field coils 401 may be arranged coaxially along the axis 405 to generate a uniform magnetic field (e.g., a static magnetic field B0) within a specific region (e.g., the region within the bore 301) when the plurality of main magnetic field coils 401 carry an electric current along a first direction. In some embodiments, the first main magnetic field coils 401-1, the second main magnetic field coils 401-2, and the third main magnetic field coils 401-3 may have the same radius or different radiuses.

The shielding coils 402 may also be arranged coaxially along the axis 405 at a larger radius from the axis 405 than the plurality of main magnetic field coils 401. That is, a radius of each of the first shielding coil 402-*a* and the second shielding coil 402-*b* may be larger than that of each of the plurality of main magnetic field coils 401. The shielding coils 402 may carry an electric current along a second direction that is opposed to the first direction. The shielding coils 402 (i.e., the first pair of shielding coils) may help shield the magnetic field generated by the plurality of main magnetic field coils 401 on a region outside the MRI apparatus.

The shielding coil group 411 may also be arranged coaxially along the axis 405 at a larger radius from the axis 405 than the plurality of main magnetic field coils 401. That is, a radius of each of the first coils 411-1 and second coils 411-2 may be larger than that of each of the plurality of main magnetic field coils 401. A direction of a current within each of the first coils 411-1 may be opposite to a direction of a current within each of the second coils 411-2. For example, each of the first coils 411-1 may include a radius designated as R1, and each of the second coils 411-2 may include a radius designated as R2, wherein R1 is greater than R2. Each of the first coils 411-1 may carry an electric current along the first direction, and each of the second coils 411-2 may carry an electric current along the second direction. That is, the direction of electric current within the first coils 411-1 (i.e., the second pair of shielding coils) may be the same as that of the plurality of main magnetic field coils 401, and the direction of electric current within the second coils 411-2 (i.e., the third pair of shielding coils) may be opposite to that of the plurality of main magnetic field coils 401 (i.e., the direction of a current within the third pair of shielding coils may be opposite to the direction of a current within the second pair of shielding coils). In some embodiments, a shielding coil of the second pair of shielding coils (i.e., a first coil 411-1) may be concentric with a shielding coil of the third pair of shielding coils (i.e., a second coil 411-2). The first coil 411-1 and the second coil 411-2 that are arranged concentrically may also be referred as a coil group of the shielding coil group 411. As shown in FIG. 4A, the shielding coil group 411 may include a first coil group and a second coil group.

In some embodiments, the shielding coil group 411 may be configured to shield the magnetic field produced by the MRI apparatus (e.g., the main magnetic field coils, the magnetic shielding coils, the gradient coils) in case that one or more components of the radiation therapy apparatus (e.g., a linear accelerator, electrons, a multi-leaf collimator) may be influenced by the magnetic field produced by the MRI apparatus on an annular region. The annular region may have the shape of an annulus with the axis 405. The annular region may include a virtual outer wall with a radius of R1 and a virtual inner wall with a radius of R2. That is, the depth of the annular region (i.e., the thickness of the annular region in the radial direction) which is defined as the distance from the virtual outer wall to the virtual inner wall in the radial direction may be equal to R1 minus R2 (R1-R2). For example, the shielding coil group 411 (e.g., the second pair of shielding coils 411-1, or the third pair of shielding coils 411-2) may be configured to shield a magnetic field between the shielding coils 402 (i.e., the first pair of shielding coils) and the main magnetic field coils 401. As another example, the shielding coil group 411 (e.g., the second pair of shielding coils 411-1, the third pair of shielding coils 411-2) may be configured to reduce a magnetic field on a region within a recess (e.g., a recess 408) of the annular cryostat 403.

In some embodiments, a magnitude of the electric current in each coil of the shielding coil group 411 may be the same, i.e., each of the first coils 411-1 may have the same magnitude of electric current as each of the second coils 411-2. Taking the first direction that is perpendicular to the X-Y plane pointing inwards as an example, the second direction may be perpendicular to the X-Y plane pointing outward. For the annular region, the magnetic field produced by the plurality of main magnetic field coils 401 (also referred to as a first magnetic field) in the annular region may be along the Y direction, and the magnetic field produced by the shielding coil group 411 (also referred to as the second magnetic field) in the annular region may be opposite to the Y direction. The magnitude of the first magnetic field may be equal to or approximately equal to the second magnetic field by adjusting the magnitude of the electric current in each coil of the shielding coil group 411 to a proper magnitude. In the proper magnitude of the electric current in each coil of the shielding coil group 411, the first magnetic field and the second magnetic field may neutralize each other such that the magnetic field in the annular region may be equal to or less than a threshold field (e.g., a zero net field). The threshold field may be set by an operator or a default setting of the radiation therapy system 100, and may be adjustable in different situations. For a region of the main magnetic field B0 that produced by the plurality of main magnetic field coils 401, the magnetic field produced by the shielding coil group 411 (also referred to as the third magnetic field) in the region of the main magnetic field B0 may be a magnetic field equal to or less than the threshold field, as the first coils 411-1 and the second coils 411-2 may produce two magnetic fields with approximate magnitudes and opposite directions in the region of the main magnetic field B0 and the two magnetic fields may neutralize each other. Thus, the main magnetic field B0 may not be influence by the protection.

As shown in FIG. 4A, the cryostat 403 may include two chambers (e.g., the left chamber and the right chamber for brevity). The two chambers may be located at opposite sides of the cryostat 403 along the axial direction (i.e., the direction of the axis 405) and may be connected by a neck portion between the two chambers. The neck portion may have a smaller radial size than the two chambers. Each chamber may have the shape of an annulus with a different outer wall. In some embodiments, the outer wall may refer to the outermost surface of each chamber that has the shape of a ring. The two chambers and the neck portion may share a same inner wall, i.e., the inner wall of the cryostat 403. In some embodiments, the inner wall may refer to the innermost surface of each chamber that also has the shape of a ring. In some embodiments, each chamber may accommodate at least one of the plurality of main magnetic field coils 401, at least one of the shielding coils 402, and at least one of the first coils 411-1 and the second coils 411-2 of the shielding coil group 411. For example, at least one of the plurality of main magnetic field coils 401 may be arranged near the inner wall of the left chamber, at least one of the shielding coils 402 (e.g., the first shielding coil 402-a) may be arranged near the outer wall of the left chamber, at least one of the first coils 411-1 and the second coils 411-2 of the shielding coil group 411 (e.g., the first coil group) may be arranged near the outer wall of the left chamber and closely to the neck portion. A gap 406 may be formed between the main magnetic field coils arranged in the left chamber and the main magnetic field coils arranged in the right chamber, allowing the radiation beam produced by the radiation therapy apparatus to pass through. The two chambers may be in fluid communication with each other through the neck portion between them. The cryostat 403 may contain cooling mediums in which the plurality of main magnetic field coils 401 and the shielding coils 402 are merged to achieve the superconducting state.

The cryostat 403 may have a recess 408 at a radial position between the inner wall of the cryostat 403 and the outer walls of the different chambers of the cryostat 403. The recess 408 may have an opening 407 formed between the outer walls of the two chambers of the cryostat 403. The recess 408 may have the shape of an annulus when viewed in a perspective view. The annulus may have same or different widths (i.e., the size in the axial direction) at different radial positions. The recess 408 may have a depth (i.e., the thickness of the annulus in the radial direction) which is defined as the distance from the opening 407 to the outermost surface of the neck portion of the cryostat 403 in the radial direction. As show in FIG. 4A, the third pair of shielding coils may be arranged close to a bottom of the recess 408, and the second pair of shielding coils may be arranged close to the opening of the recess 408.

The recess 408 may be configured to accommodate the components of the radiation therapy apparatus. As shown in FIG. 4A, the recess 408 may accommodate at least a portion of a radiation source, wherein the radiation source includes a linear accelerator 409, a collimator 412, a target 404 and a multi-leaf collimator (MLC) 410.

The linear accelerator 409 may be configured to accelerate charged subatomic particles or ions to a high speed. In some embodiments, the linear accelerator 409 may accelerate electrons using microwave technology. For example, the linear accelerator 409 may accelerate electrons in an electron beam with energy group between 4 MeV to 22 MeV using high RF electromagnetic waves.

The linear accelerator 409 may be mounted to a gantry or a drum (e.g., the gantry 306 or the drum 312) that is capable of rotating around the axis 405 and may enable the radiation beam to be emitted from a certain range of the circumferential positions, or an arbitrary circumferential position. As shown in FIG. 4A, the gantry or the drum may rotate to a first position where the linear accelerator 409 may be located above the axis 405. The linear accelerator 409 may include an accelerating waveguide (tube) whose axis is perpendicular to the axis 405. The accelerating waveguide (tube) may provide a linear path for accelerating the electrons along a beam path that is perpendicular to the axis 405. The one skilled in the art could readily understand that electrons described herein could be replaced by other particles in other embodiments.

The target 404 may be configured to receive the accelerated charged subatomic particles or ions (e.g., an electron beam) to produce the radiation beam for the therapeutic radiation. For example, the electron beam may collide with the target 404 to generate high-energy X-rays according to the bremsstrahlung effect. In some embodiments, the target 404 may be located near the exit window of the linear accelerator 409 to receive the accelerated electron beam. In some embodiments, the target 404 may be made of materials including aluminum, copper, silver, tungsten, or the like, or any combination thereof. Alternatively, the target 404 may be made of composite materials including tungsten and copper, tungsten and silver, tungsten and aluminum, or the like, or any combination thereof. The one skilled the art could readily understand that the target is not necessary for the treatment using the electron beam.

The radiation beam from the target 404 may pass through the collimator 412 to form a beam with a specific shape (e.g., cone beam). In some embodiments, the collimator 412 may include a primary collimator, a flattening filter and at least one secondary collimator.

The MLC 410 may be configured to reshape the radiation beam. For example, the MLC 410 may adjust the irradiating shape, the irradiating area, etc., of the radiation beam. The MLC 410 may be placed anywhere on the path of the radiation beam. For example, the MLC 410 may be placed close to the linear accelerator 409 as shown in FIG. 4A. Thus, the radiation beam, after being reshaped by the MLC 410, may further pass through the neck portion of the cryostat 403 and the gap 406 between the plurality of main magnetic field coils to arrive at the treatment region. As another example, the MLC 410 may be placed at a relatively long distance away from the linear accelerator (e.g., as such that the MLC 410 may be closer to, e.g., the patient to be radiated.

The MLC 410 may stay fixed relative to the linear accelerator 409, thus rotating together with the linear accelerator 409 around the axis 405. The MLC 410 may include a plurality of individual leaves of high atomic numbered materials (e.g., tungsten) moving independently in and out of the path of the radiation beam in order to block it. The shape of the radiation beam may vary when the plurality of individual leaves move in and out, forming different slots that could adapt the cross section of the tumor viewed from an axis of the radiation beam (i.e., the vertical dotted line 416 shown in FIG. 4A). In some embodiments, the MLC 410 may include one or more layers of leaves. For example, the MLC 410 may have only one layer of leaves and the height of the MLC 410 along the axis of the radiation beam from the top of the MLC 410 to the bottom of the MLC 410 may be between 7 and 10 centimeters. For another example, the MLC 410 may include two layers and the height of the MLC 410 may be at least 15 centimeters.

As shown in FIG. 4A, the radiation therapy apparatus may be located coaxially and/or radially between the first coil group and the second coil group. The radiation therapy apparatus may rotate within the annular region such that all components of the radiation therapy apparatus (e.g., the linear accelerator 409, the collimator 412, the target 404, the MLC 410) may not be influenced by the magnetic field produced by the MRI apparatus as possible. The depth of the annular region (i.e., R1-R2) may be equal to or greater than a height of a portion of the radiation therapy apparatus (e.g., a height of at least a portion of the radiation source) which is defined as the distance from the top of the portion of the radiation therapy apparatus to the bottom of the portion of radiation therapy apparatus in the radial direction.

In some embodiments, the depth of the annular region may only accommodate a portion of components of the radiation therapy apparatus to protect the portion of components from being influenced by the magnetic field produced by the MRI apparatus as possible. For example, the annular region may accommodate the target 404, the collimator 412 and the MLC 410. The linear accelerator 409 may be out of the annular region, as the accelerating waveguide (tube) of the linear accelerator 409 may be surrounded by a shielding structure or the linear accelerator 409 may be located in a relatively long distance away from the plurality of main magnetic field coils 401. The shielding structure may include a plurality of shielding layers to shield the magnetic field produced by the MRI apparatus in case that the electrons may be influenced by the magnetic field and/or absorb the radiation produced by the radiation beam of the linear accelerator 409 in case that the plurality of main magnetic field coils 401 is influenced. As another example, the annular region may accommodate the linear accelerator 409 and the target 404. The collimator 412 and the MLC 410 may be out of the annular region. More descriptions of therapeutic apparatus may be found in International Application No. PCT/CN2018/115394 entitled "RADIATION THERAPY SYSTEM AND METHOD," filed Nov. 14, 2017, the contents of which are hereby incorporated by reference.

Figure 4B:
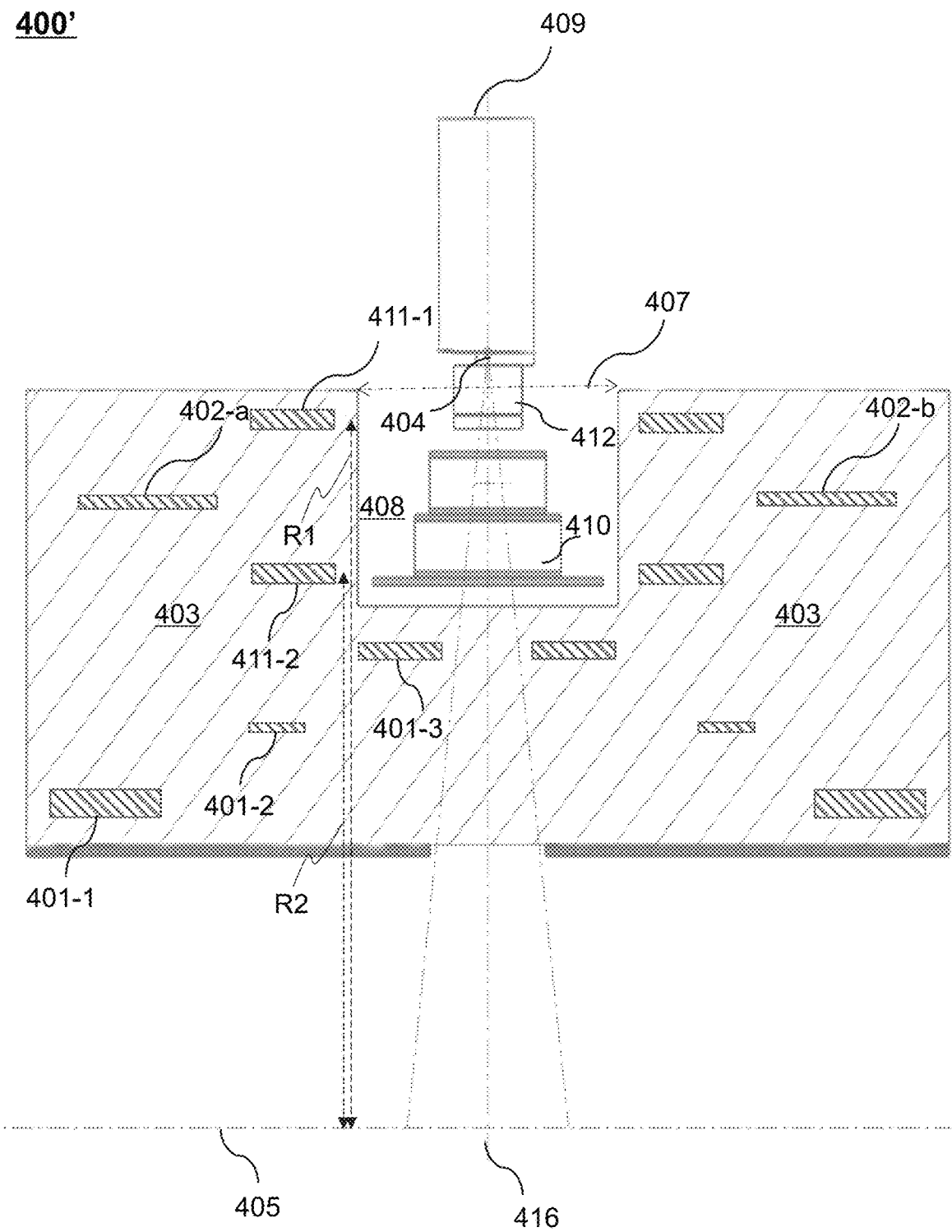
FIG. 4B shows an upper portion of a cross-sectional view of another exemplary therapeutic apparatus viewed along the Z direction according to some embodiments of the present disclosure.

FIG. 4B shows an upper portion of a cross-sectional view of an exemplary therapeutic apparatus 400' viewed along the Z direction according to some embodiments of the present disclosure. Compared with the therapeutic apparatus 400 described in FIG. 4A, at least part of the linear accelerator 409 of the therapeutic apparatus 400 may be located at the outside of the recess 408 along the radial direction of the cryostat 403, and a radius of each of the shielding coils 402 may range from R1 to R2. As shown in FIG. 4B, the linear accelerator 409 and the target 404 may stretch out of the opening 407 formed by the outer walls of the cryostat 403. The collimator 412 and the MLC 410 may be accommodated within the annular region in case the collimator 412 and the MLC 410 is influenced by the magnetic field produced by the plurality of main magnetic field coils. In some embodiments, the linear accelerator 409 may be supported by or mounted to a gantry or a drum (e.g., the gantry 306 or the drum 312) that is capable of rotating around the axis 405. More descriptions of the therapeutic apparatus 400 may be found elsewhere in the present disclosure (e.g., FIGS. 5-7 and the descriptions thereof).

Figure 4C:
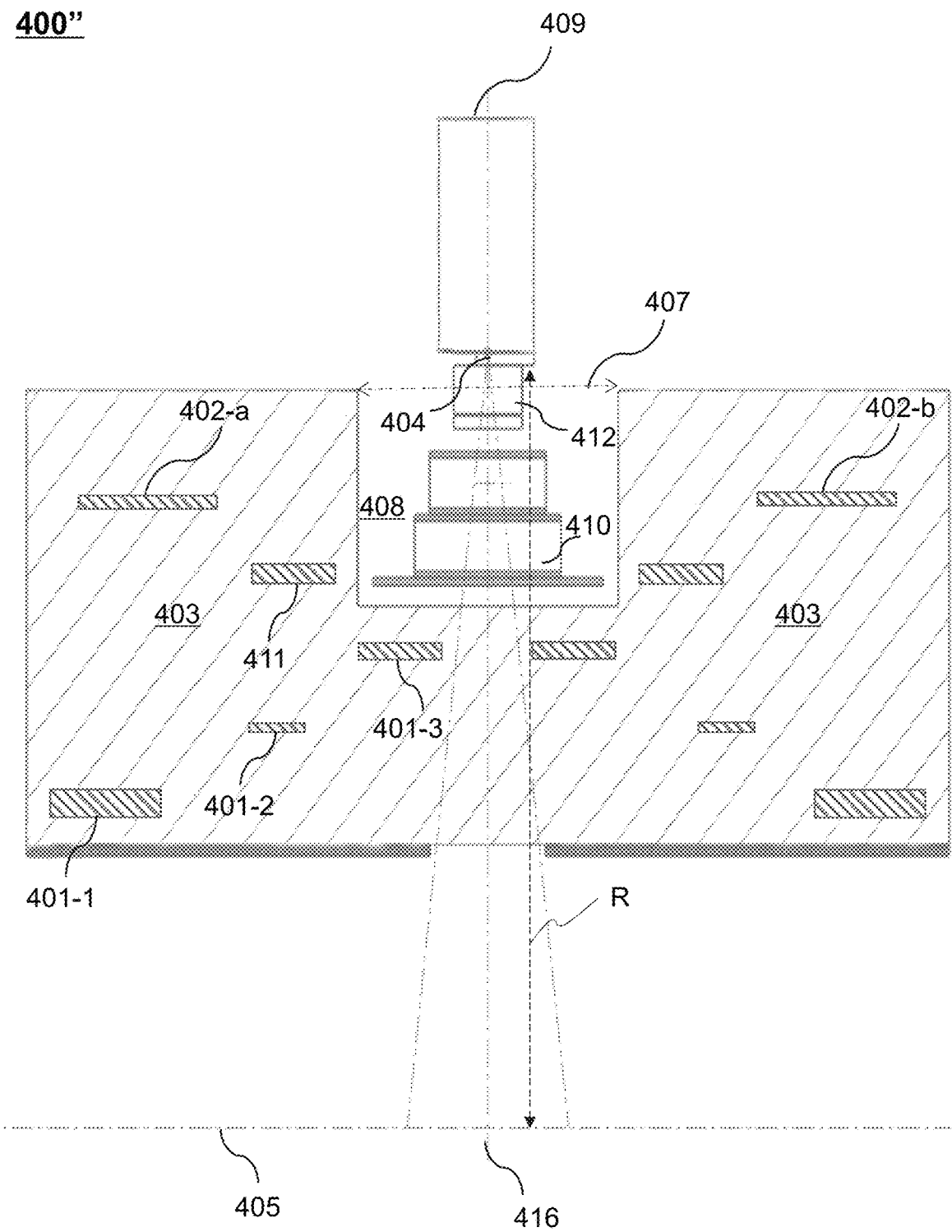
FIG. 4C shows an upper portion of a cross-sectional view of another exemplary therapeutic apparatus viewed along the Z direction according to some embodiments of the present disclosure.

FIG. 4C shows an upper portion of a cross-sectional view of another exemplary therapeutic apparatus 400" viewed along the Z direction according to some embodiments of the present disclosure. The therapeutic apparatus 400" may include an MRI apparatus that is configured to generate MRI data and a radiation therapy apparatus that is configured to apply therapeutic radiation.

As shown in FIG. 4C, the MRI apparatus may include a main magnet body and a plurality of shielding coils. For illustration, the main magnet body may include a plurality of main magnetic field coils 401 (e.g., first main magnetic field coils 401-1, second main magnetic field coils 401-2, third main magnetic field coils 401-3), and the MRI apparatus may also include a cryostat 403. The plurality of main magnetic field coils 401 and the plurality of shielding coils may be accommodated in the cryostat 403 and maintained in the superconductive state under a certain condition (e.g., when both the coils are merged in a cooling medium in the cryostat 403). The plurality of shielding coils may include shielding coils 402 and a shielding coil group 411. The shielding coils 402 may include a first pair of shielding coils with a first size, i.e., a first shielding coil 402-a and a second shielding coil 402-b. The shielding coil group 411 may include a second pair of shielding coils with a second size. The first size and the second size may be the same as or different from each other.

In some embodiments, the main magnetic body and one or more of the plurality of shielding coils (e.g., the shielding coil group 411) may be not limited to a coil type, and may be any other types including, for example, a permanent magnet, a resistive electromagnet, etc.

In some embodiments, the shielding coils 402 (i.e., the first pair of shielding coils) may be configured to shield a magnetic field outside the MRI apparatus. The shielding coil group 411 (i.e., the second pair of shielding coils) may be configured to generate a magnetic field to reduce and/or shield a magnetic field in a particular region (e.g., a region surrounding the treatment head of the radiation therapy apparatus) of the therapeutic apparatus 400".

Compared with the MRI apparatus 400 described in FIG. 4A, the shielding group 411 in FIG. 4C may include only one pair of shielding coils while the shielding group 411 in FIG. 4A includes two pairs of shielding coils. Both the shielding group 411 in FIG. 4C and the shielding group 411 in FIG. 4C may be configured to shield the magnetic field produced by the MRI apparatus (e.g., the main magnetic field coils, the magnetic shielding coils, the gradient coils) in case that one or more components of the radiation therapy apparatus (e.g., a linear accelerator, electrons, a multi-leaf collimator) may be influenced by the magnetic field produced by the MRI apparatus on the annular region that accommodates at least a portion of a radiation source of the radiation therapy apparatus.

In some embodiments, a direction of electric current within the shielding coil group 411 may be the same as or different from a direction of electronic current within the shielding coils 402. The main magnetic coils 401 may carry an electric current along a first direction and the shielding coils 402 may carry an electric current along a second direction. The first direction is opposite to the second direction as described in FIG. 4A. Merely by way of example, if the second size is equal to the first size, the shielding coil group 411 may carry an electronic current along the first direction, which is opposite to that of the shielding coils 402. The electronic current within the shielding coil group 411 may be adjusted to a proper magnitude to achieve that a magnetic field within the annular region is equal to or less than a threshold field, such that one or more components of the radiation therapy apparatus (e.g., a linear accelerator, electrons, a multi-leaf collimator) may not be influenced as possible. As another example, both the second size and the electronic current within the shielding coil group 411 may be adjusted to proper magnitudes to achieve that the magnetic field within the annular region is equal to or less than the threshold field. Merely by way of example, if the shielding coil group 411 is arranged close to a bottom of the recess 408, a current within the shielding coil group 411 may be opposite to the first direction. If the shielding coil group 411 is arranged close to an opening of the recess 408, a current within the shielding coil group 411 may be along the first direction In some embodiments, a distance (e.g., denoted by R as illustrated in FIG. 4C) from the axis 405 to the target 404 of the radiation therapy apparatus may be reduced to be a normal source-axis distance (e.g., less than or equal to 1 meter) with the shielding coil group 411, while the distance from the axis 405 to the target 404 of the radiation therapy apparatus may be larger than the normal source-axis distance (e.g., 1 meter) without the shielding coil group 411.

It should be noted that the above description of the therapeutic apparatus 400, 400' or 400" is merely provided for the purposes of illustration, and not intended to limit the scope of the present disclosure. For persons having ordinary skills in the art, multiple variations and modifications may be made under the teachings of the present disclosure. For example, the collimator 412 and the MLC 410 may be integrated to form a single collimator. As another example, the neck portion illustrated in the cryostat 403 may not form an entire annulus. Specifically, the neck portion may be discrete arcs that connect the left chamber and the right chamber of the cryostat 403. Therefore, the neck portion may intermittently appear in the path of the radiation beam when the linear accelerator 409 rotates around the axis 405 to generate the radiation beam. As still another example, the shielding coil group 411 may include more than two groups of coils as disclosed in the present disclosure, e.g., a third coil group may be added for achieving shielding the magnetic field in the annular region. As still another example, the shielding coil group 411 may include more than two pairs of shielding coils as disclosed in the present disclosure, e.g., a fourth pair of shielding coils may be added for achieving shielding the magnetic field in the annular region. The fourth pair of shielding coils may be concentric and/or coaxial with the second pair of shielding coils or third pair of shielding coils.

In some embodiments, the main magnetic body 302 may be a separated magnetic body. For example, the main magnetic body 302 may include at least two separated parts. At least portion of the coils in the main magnetic body 302 (e.g., the first shielding coil 402-a, the first coil 411-1, the first main magnetic field coils 401-1, the second main magnetic field coils 401-2, the third main magnetic field coils 401-3, etc.) may be located in one part, and the rest of the coils in the main magnetic body 302 may be located in the other part.

Figure 5A:
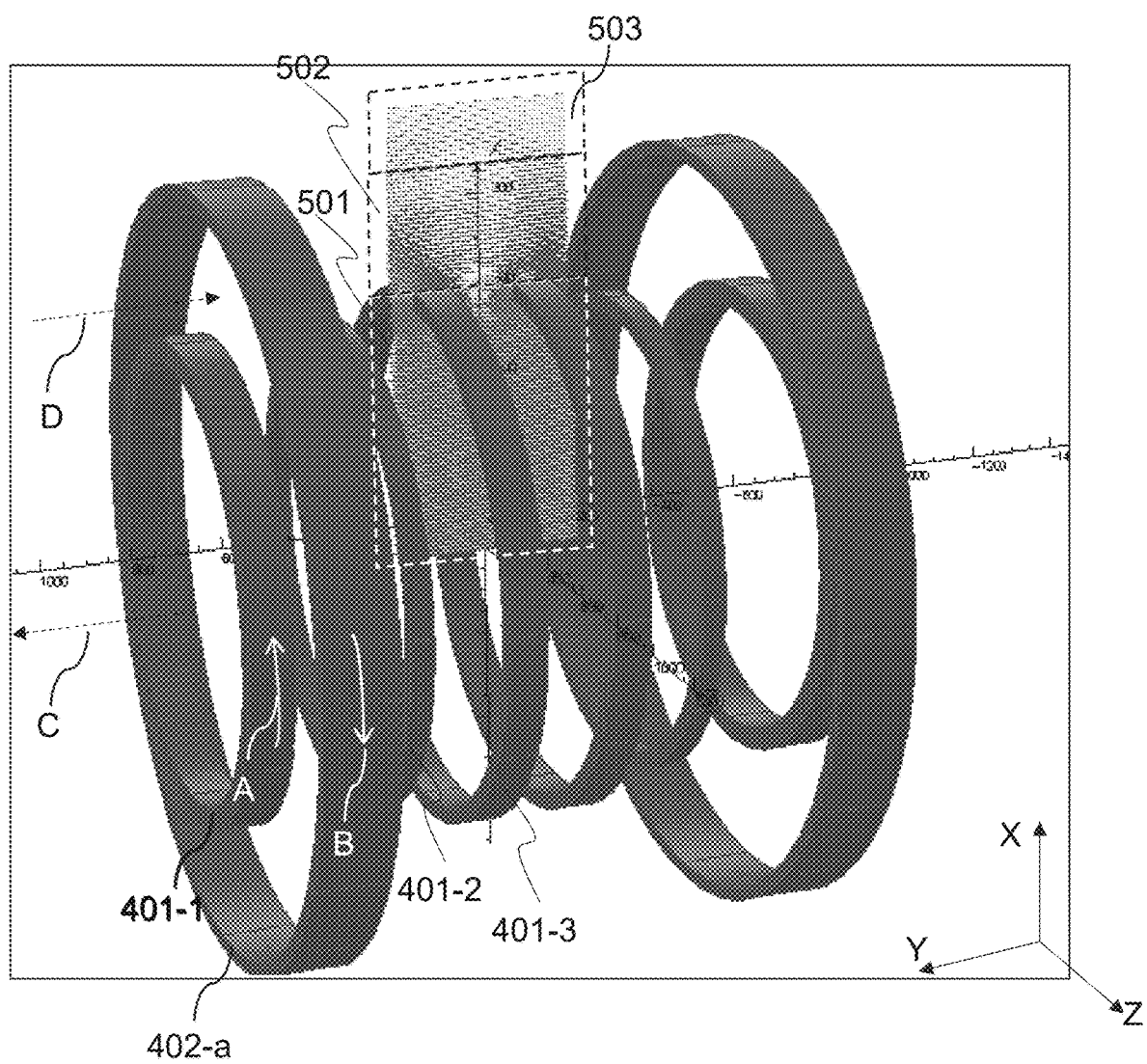
FIG. 5A shows a schematic diagram illustrating exemplary magnetic fields produced by a plurality of main magnetic field coils without a shielding coil group according to some embodiments of the present disclosure.

FIG. 5A shows a schematic diagram illustrating exemplary magnetic fields produced by a plurality of main magnetic field coils without a shielding coil group according to some embodiments of the present disclosure. As described in connection with FIG. 4A or FIG. 4B, as shown in FIG. 5A, the plurality of main magnetic field coils 401 (e.g., main magnetic field coils 401-1, main magnetic field coils 401-2, main magnetic field coils 401-3) and the shielding coils 402 (e.g., the first shielding coil 402-a, the second shielding coil 402-b) may be coaxially arranged along an axis (e.g., the axis 405). Merely by way of example, a direction of the current within each of the plurality of main magnetic field coils 401 may be designated as the first direction the same as illustrated by arrow A, and a direction of the current within each of the shielding coils 402 may be designated as the second direction the same as illustrated by arrow B. The first direction is opposite to the second direction.

In some embodiments, the main magnetic field B0 produced by the plurality of main magnetic field coils 401 may be represented by dotted box 501, the magnetic field in a middle region between the plurality of main magnetic field coils 401 and the shielding coils 402 (also referred to as a middle magnetic field) may be represented by dotted box 502, and the magnetic field in an outside region out of the shielding coils 402 (also referred to as an outside magnetic field) may be represented by dotted box 503. The middle magnetic field may be a superposition of the magnetic field produced by the plurality of main magnetic field coils 401 within the middle region and the magnetic field produced by the shielding coils 402 within the middle region. The outside magnetic field may be a neutralization of the magnetic field produced by the plurality of main magnetic field coils 401 within the outside region and the magnetic field produced by the shielding coils 402 within the outside region. The shade of the color within a dotted box may indicate a strength and distribution of the corresponding magnetic field. As shown in FIG. 5A, the main magnetic field B0 may be the strongest and distribute uniformly with a direction the same as illustrated by arrow C, the middle magnetic field may be weak and distribute non-uniformly with a direction the same as illustrated by arrow D, and the outside magnetic field may be the weakest with a direction the same as illustrated by arrow C.

Figure 5B:
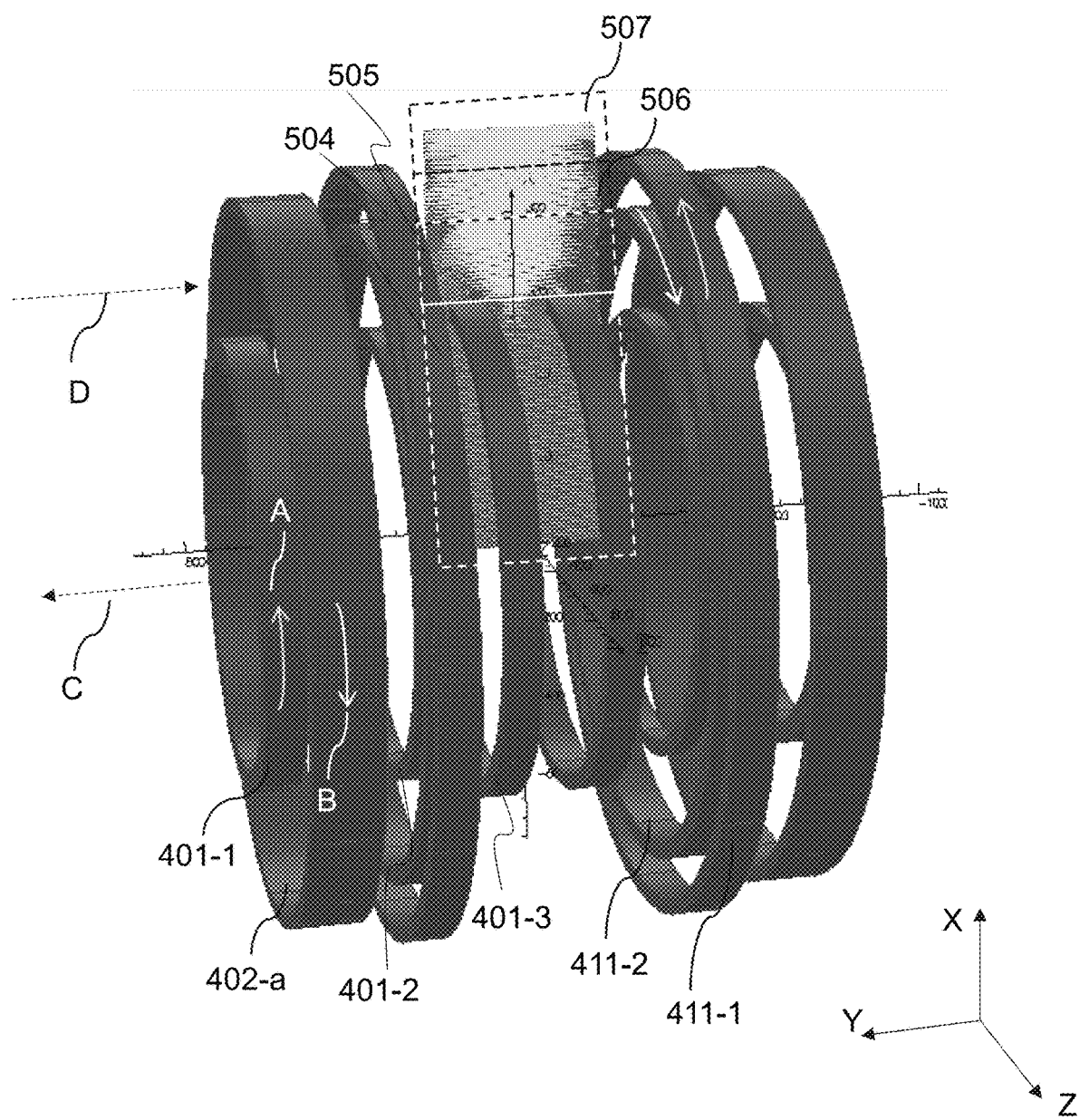
FIG. 5B shows a schematic diagram illustrating exemplary magnetic fields produced by a plurality of main magnetic field coils with a shielding coil group according to some embodiments of the present disclosure.

FIG. 5B shows a schematic diagram illustrating exemplary magnetic fields produced by a plurality of main magnetic field coils with a shielding coil group according to some embodiments of the present disclosure. As described in connection with FIG. 4B and FIG. 5A, as shown in FIG. 5B, the shielding coil group 411(e.g., the first coils 411-1 and the second coils 411-2) may be coaxially arranged with the plurality of main magnetic field coils 401 and the shielding coils 402 along an axis (e.g., the axis 405). Merely by way of example, a direction of the current within each of the first coils 411-1 may be the same as the first direction illustrated by arrow A, and a direction of the current within each of the second coils 411-2 may be the same as the second direction illustrated by arrow B. A magnitude of the current within each of the first coils 411-1 may be the same as a magnitude of the current within each of the second coils 411-2.

As shown in FIG. 5B, the main magnetic field B0 produced by the plurality of main magnetic field coils 401 may be represented by dotted box 504, the magnetic field in a middle region between the plurality of main magnetic field coils 401 and the second coils 411-2 (also referred to as a middle magnetic field) may be represented by dotted box 505, the magnetic field in the annular region between the first coils 411-1 and the second coils 411-2 (also referred to as a annular magnetic field) may be represented by dotted box 506, and the magnetic field in an outside region out of the first coils 411-1 (also referred to as an outside magnetic field) may be represented by dotted box 507. The shade of the color within a dotted box may indicate a strength and distribution of the corresponding magnetic field. In comparison with FIG. 5A, the main magnetic field B0 in FIG. 5B may still be the strongest and distribute uniformly with a direction the same as illustrated by arrow C, similar to the corresponding magnetic field in FIG. 5A, and the middle magnetic field, the annular magnetic field and the outside magnetic field in FIG. 5B may all be weaker than the corresponding magnetic field in FIG. 5A.

Figure 6A:
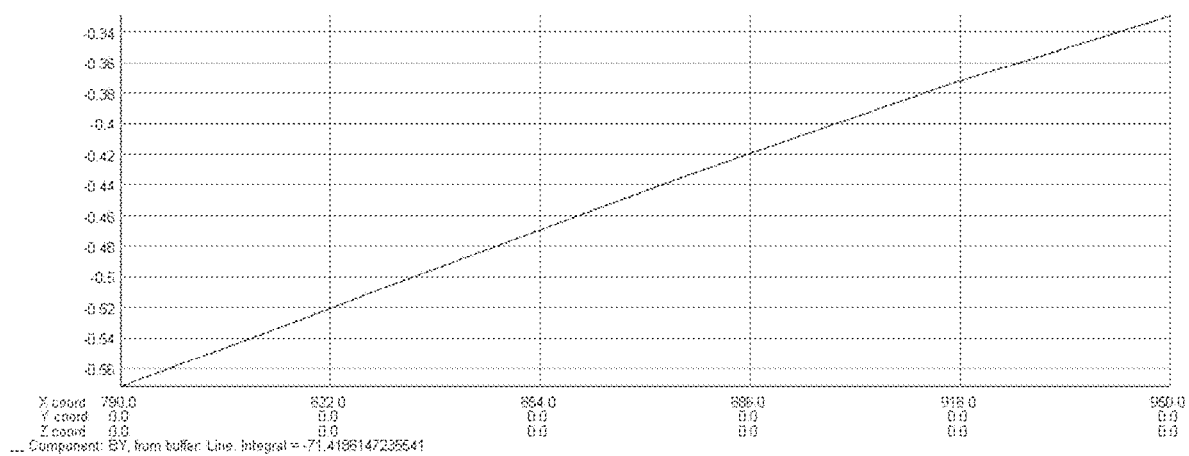
FIG. 6A shows a schematic diagram illustrating an exemplary curve of the magnetic field in the annular region without a shielding coil group according to some embodiments of the present disclosure.

FIG. 6A shows a schematic diagram illustrating an exemplary curve of the magnetic field in the annular region without a shielding coil group according to some embodiments of the present disclosure. As shown in FIG. 6A, for a requirement of the main magnetic field B0 to be 1.5 T, a magnitude of the magnetic field in the annular region without the shielding coil group 411 may range from 0.56 T to 0.35 T. A strength of the magnetic field in the annular region that is further away from the plurality of main magnetic field coils 401 may be lower than that of the magnetic field in the annular region that is closer to the plurality of main magnetic field coils 401.

Figure 6B:
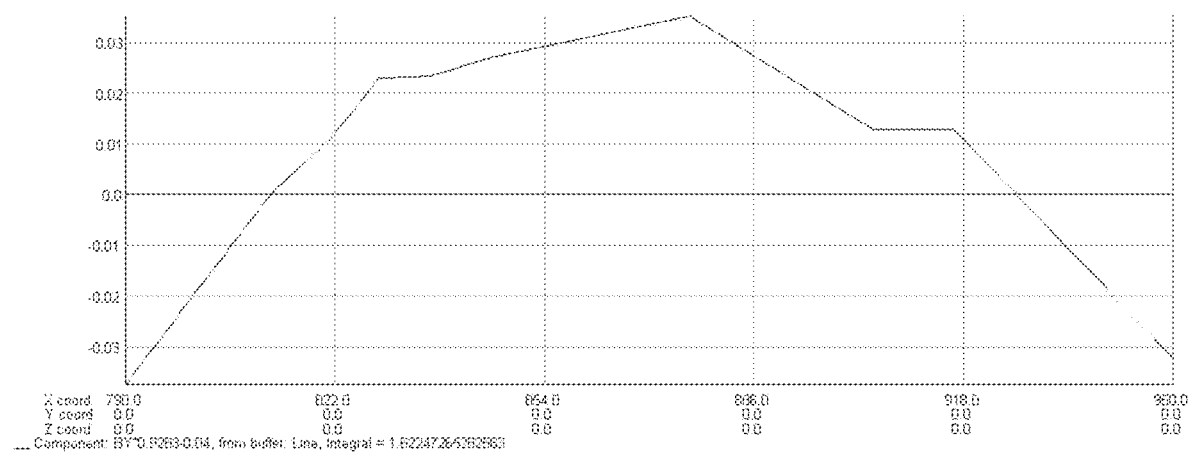
FIG. 6B shows a schematic diagram illustrating an exemplary curve of the magnetic field in the annular region with a shielding coil group according to some embodiments of the present disclosure.

FIG. 6B shows a schematic diagram illustrating an exemplary curve of the magnetic field in the annular region with a shielding coil group according to some embodiments of the present disclosure. As described in connection with FIG. 5 and FIG. 6A, a magnitude of the magnetic field in the annular region with the shielding coil group 411 as shown in FIG. 6B may range from 0 to 0.04 T, which is lower than that of the magnetic field in the annular region without the shielding coil group 411 as shown in FIG. 6A. By adding the shielding coil group 411 in the MRI apparatus, one or more components of the radiation therapy apparatus received within the annular region may not be influenced by the magnetic field produced by the MRI apparatus as possible.

Figure 7:
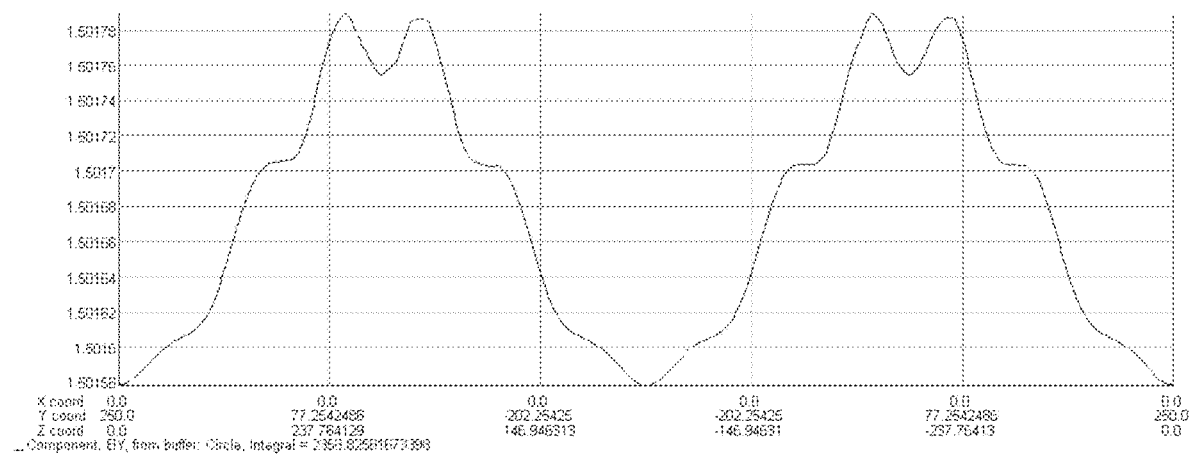
FIG. 7 shows a schematic diagram illustrating an exemplary curve of the main magnetic field B0 in the MRI apparatus with a shielding coil group according to some embodiments of the present disclosure.

FIG. 7 shows a schematic diagram illustrating an exemplary curve of the main magnetic field B0 in the MRI apparatus with a shielding coil group according to some embodiments of the present disclosure. As described in connection with FIG. 5 and FIG. 6, a magnitude of the magnetic field B0 in MRI apparatus with the shielding coil group 411 may keep around 1.5 T. By adding the shielding coil group 411 in the MRI apparatus, the plurality of main magnetic field coils 401 of the MRI apparatus may not increase power consumption, and the magnitude of the main magnetic field B0 in the MRI apparatus may not be influenced by the shielding coil 411.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A therapeutic apparatus including a magnetic resonance imaging (MRI) apparatus configured to acquire MRI data with respect to a region of interest (ROI), the MRI apparatus including:
   a main magnet body including a plurality of main magnetic field coils coaxially arranged along an axis; and
   a plurality of shielding coils including a first shielding coil, a second shielding coil and a shielding coil group arranged coaxially along the axis, wherein the shielding coil group is located between the first shielding coil and a second shielding coil.

2. The apparatus of claim 1, wherein the shielding coil group includes a first coil group and a second coil group arranged coaxially along the axis.

3. The apparatus of claim 2, wherein the first coil group or the second coil group includes a first coil and a second coil.

4. The apparatus of claim 3, wherein the first coil and the second coil are arranged concentrically.

5. The apparatus of claim 3, wherein a direction of a current within the first coil is opposite to a direction of a current within the second coil.

6. The apparatus of claim 3, wherein a radius of the first coil or the second coil is larger than that of the plurality of main magnetic field coils.

7. The apparatus of claim 3, wherein a radius of the first coil is greater than a radius of the second coil.

8. The apparatus of claim 3, further comprising an annular cryostat, wherein the annular cryostat includes:
   at least one outer wall and at least one inner wall coaxial around the axis; and
   an annular recess between the at least one outer wall and the at least one inner wall, wherein the annular recess has an opening formed at the at least one outer wall.

9. The apparatus of claim 8, wherein the annular recess is located coaxially between the first coil group and the second coil group.

10. The apparatus of claim 8, wherein at least portion of the annular recess is located radially between the first coil and the second coil.

11. The apparatus of claim 8, further comprising:
   a radiation therapy apparatus configured to apply therapeutic radiation to at least one portion of the ROI, the radiation therapy apparatus including:
      a linear accelerator configured to accelerate electrons in an electron beam to produce a photon beam of the therapeutic radiation, the linear accelerator being at least partially located within the annular recess of the annular cryostat; and
      one or more collimation components configured to shape the photon beam of the therapeutic radiation.

12. The apparatus of claim 11, wherein at least portion of the radiation therapy apparatus is located coaxially between the first coil group and the second coil group.

13. The apparatus of claim 11, wherein at least portion of the radiation therapy apparatus is located radially between the first coil and the second coil.

14. A magnetic resonance imaging (MRI) apparatus configured to acquire MRI data with respect to a region of interest (ROI), the MRI apparatus being configured to be arranged coaxially with a radiation therapy apparatus along an axis, the MRI apparatus including:
   a plurality of main magnetic field coils coaxially arranged along an axis; and
   a plurality of shielding coils arranged coaxially along the axis, wherein the plurality of shielding coils are configured to reduce a magnetic field in a path of rotation of at least a portion of a radiation source of the radiation therapy apparatus; and
   the shielding coils include a first coil and a second coil with different sizes, wherein a direction of a current within the first coil is opposite to a direction of a current within the second coil.

15. The apparatus of claim 14, wherein a radius of the first coil is greater than a radius of the second coil which is concentric with the first coil.

16. The apparatus of claim 15, wherein the direction of the current within the first coil is the same as a direction of a current within the main magnetic field coils.

17. A magnetic resonance imaging (MRI) apparatus configured to acquire MRI data with respect to a region of interest (ROI), the MRI apparatus including:
   an annular cryostat;
   a plurality of main magnetic field coils coaxially arranged along an axis of the annular cryostat;
   at least a first pair of shielding coils and a second pair of shielding coils with different sizes, wherein
      a direction of a current within the first pair of shielding coils is opposite to a direction of a current within the main magnetic field coils,
      the first pair of shielding coils is configured to shield a magnetic field outside the MRI apparatus, and
      the second pair of shielding coils is configured to shield a magnetic field between the first pair of shielding coils and the main magnetic field coils.

18. The apparatus of claim 17, wherein a direction of a current within the second pair of shielding coils is the same as the direction of a current within the main magnetic field coils, the second pair of shielding coils being close to the first pair of shielding coils.

* * * * *